United States Patent [19]

Shoup

[11] 4,123,098
[45] Oct. 31, 1978

[54] CONTACT LENS INSERTION AND RETRACTION DEVICE

[76] Inventor: Leo E. Shoup, 125 N. Mt. Vernon, Prescott, Ariz. 86301

[21] Appl. No.: 818,435

[22] Filed: Jul. 25, 1977

[51] Int. Cl.² ............................................. A61F 9/00
[52] U.S. Cl. .................................. 294/1 CA; 294/64 R
[58] Field of Search ............ 294/1 CA, 64 R; 15/422; 128/303 R; 206/5.1; 351/160

[56] References Cited

U.S. PATENT DOCUMENTS

| | | | |
|---|---|---|---|
| 428,246 | 5/1890 | Fay | 294/64 R X |
| 1,035,846 | 8/1912 | Beaver | 294/64 R X |
| 1,990,334 | 2/1935 | Koppe | 294/64 R |
| 2,384,334 | 9/1945 | Olson | 294/1 CA X |
| 2,919,696 | 1/1960 | Rinaldy | 294/1 CA X |
| 3,129,971 | 4/1964 | Kobler | 294/64 R |
| 3,424,486 | 1/1969 | Corley | 294/1 CA X |
| 3,645,576 | 2/1972 | Horres | 294/1 CA |
| 3,879,076 | 4/1975 | Barnett | 294/64 R X |

*Primary Examiner*—Johnny D. Cherry
*Attorney, Agent, or Firm*—Harry Max Weiss

[57] ABSTRACT

This disclosure relates to a contact lens insertion and retraction device which is especially useful for either inserting or retracting a soft contact lens, onto or from the surface of a person's eye. This device utilizes a flexible bulb member, in cooperative combination with an attached tubular-shaped member, for supplying negative (suction) or positive (exhaust) pressure on a contact lens holder portion that is attached to the open or other end of the tubular-shaped member and thereby connected to the flexible bulb member. During the operation of removing the contact lens from the eye, a negative pressure or suction is applied to the contact lens from the contact lens holder portion by squeezing the flexible bulb member. The flexible bulb member also supplies an exhaust pressure on the contact lens by means of inserting the contact lens onto the eye. The contact lens holder portion is removable for asepticizing. Additional features include angling the contact lens holder portion with its attached tubular-shaped member at a preferred angle to permit, through use of a mirror, good visual observation of the insertion and extraction operations. A circular-shaped cavity with a diagonal blocking member is utilized at the end of the contact lens holder portion for optimizing the application of suction and exhaust pressures from the flexible bulb portion to the back portion of the contact lens during the insertion and extraction operations.

4 Claims, 4 Drawing Figures

CONTACT LENS INSERTION AND RETRACTION DEVICE

BACKGROUND OF THE INVENTION

1. Field of the Invention

This invention generally relates to contact lens insertion and extraction devices and, more particularly, relates to contact lens insertion and extraction devices especially useful for soft contact lenses.

2. Description of the Prior Art

In the past, several prior art devices have been disclosed for the purpose of inserting and/or removing a contact lens. For example, U.S. Pat. No. 2,919,696 discloses a ram type device which is spring loaded and is used to insert a contact lens on an eye. One embodiment of this patent shown a bulb member which is used to apply a suction on the connecting tube for the purpose of removing a contact lens. This prior art device does not permit good visual indication of the contact lens during insertion or extraction operations with a mirror, does not have a means of preventing a soft contact lens from being sucked down the connecting tube during the extraction operation using the bulb, and cannot have the contact lens holder portion easily asepticized which is very important for soft contact lens use.

U.S. Pat. Nos. 3,177,874 and 3,091,328 disclose a contact lens applicator device and a contact lens inserter and remover device, respectively. The applicator device of U.S. Pat. No. 3,177,874 is not designed for removing a contact lens, does not have any means of preventing a soft contact lens from being sucked down the connecting tube, and cannot have the contact lens holder portion easily asepticized. The contact lens inserter and remover device of U.S. Pat. No. 3,091,328 is a fairly complex structure which uses both springs and a suction type bulb, does not permit good visual observation of the insertion and extraction operations, does not permit easy asepticizing of the contact lens holder, and does not provide a good gripping action on the back portion of the contact lens.

U.S. Pat. No. 3,424,486 discloses another contact lens handling device which uses a suction cup and a bulb type member for applying suction pressure to the suction cup. This device has a ninety degree bend to permit better visual observation of the contact lens handling operation with a mirror. The contact lens holder portion can be removed from the rest of the device, but the contact lens holder portion could not be used for a soft contact lens as there are no means for preventing a soft contact lens from being sucked down the connecting tube during the process of applying suction into the back of the soft contact lens.

U.S. Pat. Nos. 2,384,334 and 3,583,010 disclose various devices using pneumatic pick up features as described above or suction type cups, but these references are not believed to be as pertinent to the art of handling contact lenses as the other references cited in this specification.

U.S. Pat. No. 3,647,380 discloses a contact lens holder which has a contact lens holder that can be reversed to either provide a concave or convex surface for handling a contact lens regardless if it is up or down. This device has the disadvantage of not being very good for use with a soft contact lens because it cannot adequately grip the back surface portion of the soft contact lens. Furthermore, the device cannot be used well with a mirror.

U.S. Pat. No. 3,934,914 discloses a fairly complex device for inserting and removing a contact lens which includes a light transmitting member and shaft as an aid in sighting through the device during operation. This device is expensive and the rather large diameter walls thereof do not permit a good visual observation of the inserting and removing operations except possibly through the relatively narrow light transmitting shaft in the center of the device.

U.S. Pat. No. 3,879,076 is a fairly complex apparatus for applying and removing a soft contact lens which utilizes a removable contact lens holder portion that contains a number of ducts to permit suction to be applied through the ducts during the applying and removing operations. This apparatus recognized that there was a major problem in handling a soft contact lens with a pneumatic type device and utilizes a very expensive type of solution, namely, a contact lens holder with longitudinal-shaped ducts to provide a gripping action on the back surface portion of the lens without having the soft contact lens be sucked down the pneumatic tube. This apparatus is not only relatively expensive and complex, but does not permit good visual view of the soft contact lens applying and removing operations. Furthermore, it is not known whether the disclosed longitudinal ducts can provide a good gripping action by the plurality of relatively point type suction contacts and whether, in use, blockage of these small diameter ducts will be a problem.

Accordingly, a need existed to provide a relatively simple, low cost contact lens handling device which would be especially useful for handling a soft contact lens and overcome the disadvantages of the above cited prior art devices.

BRIEF DESCRIPTION OF THE DRAWING

Referring to FIG. 1, reference numeral 10 generally depicts the contact lens insertion and retraction device of this invention. This device 10 has a flexible bulb member 12 preferably made of rubber or some other equivalent type of flexible material. Preferably, the flexible bulb member 12 is a four ounce capacity flexible rubber bulb.

Figure 1:
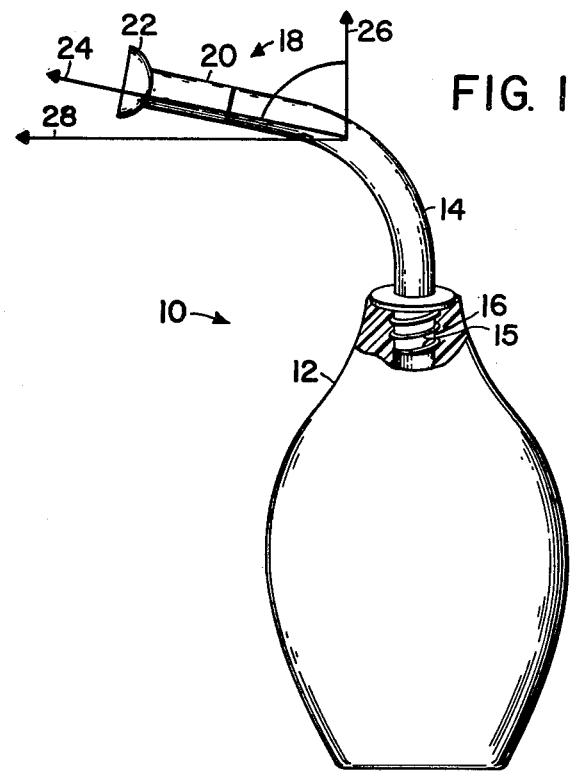
FIG. 1 is a side elevational view of the contact lens inserting and retracting device of this invention showing the flexible bulb member, the angled, thin, connecting tubular-shaped member, and the removable contact lens holder portion.

Attached to the top end portion of the flexible bulb member 12 is a thin, angled, connecting tubular-shaped member 14 which is preferably made of plastic and has a threaded end 15 which screws into an internally threaded portion 16 located at the top end portion of the flexible bulb member 12. The threaded male connecting portion 15 functions to removably connect the connecting tubular-shaped member 14 to the threaded portion 16 of the flexible bulb member 12.

Connected to the connecting tubular member 14 is a contact lens holder portion 18 which has a tubular element 20 that is connected to the connecting tubular member 14. The contact lens holder portion 18 also has a cup-shaped element 22 which is preferably integrally connected to the connecting tubular member 14.

As can be seen with respect to FIG. 1, the upper portion of the connecting tubular member 14 with the connected contact lens holder portion 18 (preferably connected in the same manner as the connecting tubular member 14 is connected to the flexible bulb member 12) together form an angle of about 75° as defined by one line 24 representing the axis of the upper portion of the connecting tubular member 14 with the connected contact lens holder portion 18 and intersecting line 26 that is perpendicular to the bottom line of the flexible bulb member 12 and is also, incidentally, the 0° line with respect to axis of the straight portion of the connecting tubular member 14 that is adjacent to the flexible bulb member 12. Line 28 represents the 90° line with respect to the line 26.

The importance of angling the connecting tubular member 14 with its attached contact lens holder portion 18 as shown by FIG. 1 is to permit good visual observation with the use of a mirror of the insertion and retraction operations while providing a good angle for facilitating insertion and removal of a soft contact lens (not shown).

Figure 2:
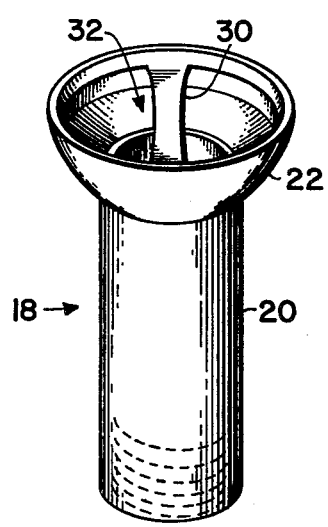
FIG. 2 is an enlarged perspective view of the contact lens holder portion of the device of FIG. 1 showing a portion of the contact lens holding cavity with its central blocking member and the connecting threads at the bottom of the contact lens holder portion for connection to the connecting tubular-shaped member.
Figure 3:
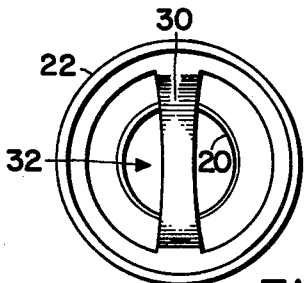
FIG. 3 is an end view looking down into the cavity of the contact lens holder portion.

Referring to FIG. 2, an enlarged view is shown of the contact lens holder portion 18 with its tubular element 20 and its cup-shaped element 22. A diagonal blocking member 30 is located within and across a substantially semicircular-shaped cavity 32 located on the inner portion of the cup-shaped element 22. The function of the diagonal blocking member 30 is to prevent a soft contact lens from being sucked down the tube formed by the tubular element 20 and the connecting tubular member 14 during insertion or retraction operations. As can be seen with respect to both FIGS. 2 and 3, the semicircular-shaped cavity 32 provides a simple, but very effective technique for providing maximum gripping or suction action around the blocking member 30 on the back surface portion of a soft contact lens which is critical during insertion and retraction operations. The shape of the semicircular-shaped cavity 32 generally conforms to the shape of the semicircular-shaped soft contact lens. The diagonal blocking member 30 is concave shaped.

Figure 4:
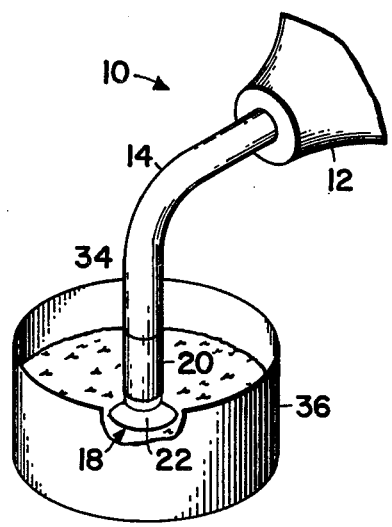
FIG. 4 is a perspective view of a portion of the device of FIG. 1 including the connecting tubular-shaped member and the contact lens holder portion inserted in a container holding a saline solution.

Referring to FIG. 4, the insertion and retraction device 10 is shown as it is used to submerge the contact lens holder portion 18 into a saline solution 34 located in a container 36. Thus, the contact lens holder portion 18 is rinsed in this manner in the saline solution 34 in order to cleanse it for use with a soft contact lens. If desired, the contact lens holder portion 18 can be removed and separately asepticized in a saline solution.

CONTACT LENS INSERTION AND RETRACTION OPERATION

In order to remove a soft contact lens from a person's eye, the insertion and retraction device 10 is held with one hand around the flexible bulb 12. The semicircular-shaped cavity 32 of the cup-shaped element 22 is positioned over the soft contact lens located on a person's eye. Prior to actual contact with the soft contact lens, suction is applied to the semicircular-shaped cavity 32 by squeezing the flexible bulb 12. Upon contact with the soft contact lens, the bulb 12 is released which causes the back or convex portion of the soft contact lens to be gripped for removal from contact with the eye. Preferably, in the process of actually removing the soft contact lens from contact with the eye, it may be desirable to tilt sideways and/or twist the insertion and retraction device 10 to lift off a portion of the soft contact lens and thereby minimize stress or pressure on the eye.

In placing the soft contact lens on a person's eye, the insertion and retraction device 10 is also held with one hand around the flexible bulb 12 and the bulb 12 is squeezed slightly to provide suction to grip the back surface portion of the soft contact lens which is usually picked off a person's hand after rinse with a saline solution. The cup-shaped element 22 with its soft contact lens located therein is positioned so as to permit the soft contact lens to be placed on the eye's pupil. Upon contact on the eye, the soft contact lens is released and applied to the eye by squeezing the flexible bulb 12 which causes air pressure to propel the soft contact lens onto the eye.

While the invention has been particularly shown and described in reference to the preferred embodiment thereof, it will be understood by those skilled in the art that changes in the form and details may be made therein without departing from the spirit and scope of the invention.

What is claimed is:

1. A soft contact lens insertion and retraction device comprising, in combination, a flexible bulb member, a thin, angled, connecting tubular member having one end connected to said flexible bulb member, a soft contact lens holder portion connected to the other end of said connecting tubular member, said soft contact lens holder portion having a cup-shaped member located at one end thereof, said cup-shaped member having a semi-circular shaped cavity, and concave blocking means extending across said semi-circular shaped cavity for preventing a soft contact lens from being sucked down in the direction of said flexible bulb member, said concave blocking means comprising a diagonally extending concave blocking member having a relatively large opening on each side thereof for permitting maximum flow of air pressure.

2. A soft contact lens insertion and retraction device in accordance with claim 1 wherein said angled connecting tubular member has an angled portion at an angle of between 45° and 90° with respect to the portion of said connecting tubular member connected to said flexible bulb member.

3. A soft contact lens insertion and retraction device in accordance with claim 2 wherein said angled portion extends at an angle of about 75° with respect to the portion of said connecting tubular member connected to said flexible bulb member.

4. A soft contact lens insertion and retraction device in accordance with claim 3 wherein said soft contact lens holder portion is removably connected to the angled portion of said connecting tubular member.

* * * * *